United States Patent [19]

Gibson et al.

[11] Patent Number: 5,302,729
[45] Date of Patent: Apr. 12, 1994

[54] DIBENZO CROWN MONOMERS AND POLYMERS FORMED THEREFROM

[75] Inventors: Harry W. Gibson; Yadollah Delaviz, both of Blacksburg, Va.

[73] Assignee: Virginia Tech Intellectual Properties, Inc., Blacksburg, Va.

[21] Appl. No.: 686,087

[22] Filed: Apr. 16, 1991

Related U.S. Application Data

[63] Continuation-in-part of Ser. No. 418,362, Oct. 6, 1989, Pat. No. 5,028,721, and a continuation-in-part of Ser. No. 574,633, Aug. 29, 1990, Pat. No. 5,142,068.

[51] Int. Cl.$^5$ ............................................. C07D 323/00
[52] U.S. Cl. ..................................................... 549/349
[58] Field of Search ........................................ 549/349

[56] References Cited

U.S. PATENT DOCUMENTS 4,876,367  10/1989  Urban .................................. 549/349
4,942,149   7/1990  Shinbo et al. ........................ 549/349

FOREIGN PATENT DOCUMENTS 0726096  4/1980  U.S.S.R. .
0763344  9/1980  U.S.S.R. .
1313856  5/1987  U.S.S.R. .

*Primary Examiner*—C. Warren Ivy
*Assistant Examiner*—A. A. Owens
*Attorney, Agent, or Firm*—Richard P. Fennelly; Louis A. Morris

[57] ABSTRACT

Novel bis(extraannular functionally-substituted phenylene) crown compounds, useful as chelating agents or in the synthesis of condensation polymers containing large semi-rigid macrocycles in the polymer backbone, are described. A broad range of functional groups (preferably in the 5-position) can be used in the 1,3-phenylene varieties. Carboxy functional groups are used in certain novel 1,2-phenylene crowns.

2 Claims, No Drawings

DIBENZO CROWN MONOMERS AND POLYMERS FORMED THEREFROM

This is a continuation-in-part of U.S. Ser. No. 418,362, filed Oct. 6, 1989 now U.S. Pat. No. 5,028,721 and of U.S. Ser. No. 574,633, filed Aug. 29, 1990 now U.S. Pat. No. 5,142,068.

BACKGROUND OF THE INVENTION

Various disclosures exist in the literature dealing with polymeric compositions containing moieties derived from linear polymer units and moieties derived from cyclic ones.

The formation of "polyrotaxanes" which are derived from the physical threading of linear molecules through macrocyclic structures has been proposed in such publications as H. W. Gibson et al., Polym. Prepr., 29(1), 248-249 (1988), P. R. Lecavalier et al., Polym. Prepr., 30(1), 189-190 (1989), and H. W. Gibson et al., Polym. Prepr., 31(1), 79-80 (1990).

The placement of a monofunctional macrocycle containing an 18 atom-sized ring (an 18-crown-6) in a polymer has been disclosed as another way of forming polymeric compositions containing structures of linear polymeric moieties and macrocyclic structures. See V. Percec et al., Polym Prepr., 30(2), 444-445 (1989).

G. W. Gokel et al., in Macrocyclic Polyether Syntheses (1982), Springer-Verlag, Berlin-Heidelberg-New York, in Tables 3.29 (pp. 149-150) and 6.4 (pp. 304-308) gives examples of a variety of polymeric crowns and crown-containing polymers and polycrowns.

Blasius et al., in Fresenius' Z. Anal. Chem. 1977, 284(5), 337-360 discuss the preparation, characterization and application of complex forming exchangers with crown compounds or cryptands as anchor groups., Various dibenzo crown-containing polymers are illustrated (e.g., structures I, III and VI-VIII on page 338.

U.S. Pat. No. 3,956,136 teaches the manufacture of various nitrogen-linked cyclic polyether ion binding polymeric liquid purification materials including those with a dibenzo crown structure (see Col. 5, lines 31-33 and Col. 7, lines 10-12). The nitrogen linkage for such materials is depicted as being on the benzo groups of the dibenzo crown and yields a nitrogen-containing backbone polymer (e.g., a polyamic acid polymer, and polyimide polymer, or a polyamide-imide polymer.

U.S. Pat. No. 4,438,251, which at Col. 1, lines 40-48 refers to the previously discussed nitrogen linkage on the dibenzo rings (i.e., a reduced nitro functionality) describes polyurethane-containing polymers including a macrocyclic crown ether in the polymer backbone. The reactive moieties on the dibenzo rings for the crown ethers shown in this patent are —CH$_2$OH which are derived by the reduction of an aldehyde group —CHO.

SUMMARY OF THE INVENTION

The instant invention, in one embodiment, relates to novel polymers which are formed by the appropriate polymerization of a polymerizable dibenzo crown macrocycle having on each benzo ring a functional group. The monomers used in the polymerization reactions described herein (and the polymers that result therefrom) are believed to be novel in certain differing aspects. All of the macrocyclic monomers described herein having extraannular (outwardly facing) substituents which can be used in polymer formation are substantially pure, i.e., mixtures of more than one position isomer of the functionalized crown are not in the product from the reaction. In many prior art techniques the functional group is derived from a moiety (e.g., NO$_2$) which is substituted onto the phenylene rings using a reaction (e.g., nitration) which gives rise to an isomer mixture as the product. Firstly, the basic crown structure is of the bis(1,3-phenylene) crown variety rather than being of the bis(1,2-phenylene) crown variety as shown in the prior art references known to the inventors. The extraannular (i.e., outwardly facing) functional substituents responsible for polymerization can be selected from a wide variety of complementary groups which can give condensation polymers for such novel bis(1,3-phenylene) crowns and are preferably in the 5-position, rather than the 4-position. The use of carboxy functional groups (e.g., carboxylic acid, ester, or halide) would even be a novel feature for such monomers if a bis(1,2-phenylene) crown structure were chosen.

DETAILED DESCRIPTION OF THE INVENTION

The invention is directed in one embodiment to polymer structures which can contain a semi-rigid macrocycle as a backbone moiety. Semi-rigidity in the macrocycle is desirably achieved by the incorporation of phenylene units in the macrocycle as further illustrated below. Macrocycle rings larger than about twenty-five carbon atoms (or of comparably sized atoms such as oxygen, nitrogen, sulfur and the like) are preferred in accordance with the present invention.

A preferred type of difunctional macrocycle is shown in U.S. Pat. No. 5,028,725, which is incorporated herein by reference. Such a macrocycle is of the formula

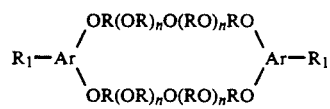

where R$_1$ denotes an appropriate functional group which can be used in a condensation polymerization reaction R is lower alkylene, such as ethylene and n can range from 1 to 5. These materials, such as bis(5-carbomethoxy-1,3-phenylene)-32-crown-10 can be formed by first reacting a functionalized dihydroxy aromatic compound with a hydroxy protecting-group-substituted halopolyether, deprotecting the resulting product to form a diol, forming the corresponding tosylate therefrom, and reacting the tosylate with the same or an analogous diol in a cyclization reaction to form the desired crown ether compound. This type of process is shown in greater detail in U.S. Pat. Nos. 5,028,721 and 5,142,068.

A more simple one-step route is described in U.S. Pat. No. 5,142,068, which is incorporated herein by reference, wherein a functionalized dihydroxy aromatic compound (e.g., orcinol monohydrate is reacted with a poly(alkylene glycol) ditosylate in organic solvent under reflux using base.

The functional groups usable in the macrocyclic monomers of the present invention can be chosen from a fairly wide range for appropriate reaction with other, conventional non-crown monomers, if desired, to form appropriate polymers. For example, listed below are some polymers which can be formed by condensation polymerization techniques:

| Polymer | Crown Monomer | Complementary Conventional Monomer |
|---|---|---|
| Polyester | $R_1$ = —COOH, —COCl, —COOR | Alkylene glycol or bisphenol |
| Polyamide | $R_1$ = —COOH, —COCl, —COOR or —$NH_2$ | Alkylene or arylene diamine or diacid derivative |
| Polyether | $R_1$ = OH | Activated aromatic dihalide |
| Polymethine | $R_1$ = —C(O)H or $NH_2$ | Alkylene or arylene diamine or dialdehyde |
| Polyurethane | $R_1$ = —$CH_2OH$ or —NCO | Alkylene or arylene diisocyanate or diol |
| Polyurea | $R_1$ = —$NH_2$ or —NCO | $COCl_2$ or $NH_2$ |
| Polycarbonate | $R_1$ = OH or OC(O)Cl | $COCl_2$ dialkylene glycol or bisphenol |

If the macrocycle monomers have a bis(1,2-phenylene) structure for the macrocycle, it is deemed that the instant invention relates to novel monomers of that type when the functional group $R_1$ is a carboxy group, such as, carboxylic acid (—COOH), carboxylic acid halide (—COX, where X is halogen such as chlorine) and carboxylic acid ester (—COR, where R is alkyl, e.g., lower alkyl).

The macrocycle monomers described herein, which can have crown sizes of from about 14 to about 78 atoms, are useful in the synthesis of the aforementioned types of polymers or as complexation agents per se.

The preceding description has shown the same "R" group (i.e., $R_1$) at either end of the macrocycle. Persons of ordinary skill in the art would realize that such monomers are "AA" type monomers. It is also within the purview of the present invention to synthesize "AB" type monomers in which the "R" groups at either end of the macrocycle differ from one another and yet are complementary in the sense of being reactible with either complementary conventional monomers, as earlier described, or even with each other (i.,e., $R_1$ and $R_2$ are selected as the respective functional groups in the macrocycle and are reactible with each other).

The Table and formula which follow give suitable direction in regard to how these AB type monomers might be configured:

| Polymer | IN AB CROWN MONOMER | |
|---|---|---|
| | $R_1$ | $R_2$ |
| Polyester | COOH, COCl, $COOR_3$ | OH, $R_4$, OH |
| Polyamide | COOH, COCl, $COOR_3$, $CONH_2$ | $NH_2$, $R_4NH_2$ |
| Polyether | OH, $R_4$OH | ZArX, $R_4$X |
| Polymethine | $NH_2$, $R_4NH_2$ | CHO, $R_4$CHO |
| Polyurethane | NCO, NHCOCl | $R_4$OH |
| Polyurea | NCO, NHCOCl | $NH_2$, $R_4NH_2$ |

$$R_1-Ar\begin{matrix}OR(OR)_nO(RO)_nRO\\ \\OR(OR)_nO(RO)_nRO\end{matrix}Ar-R_2$$

$R_3$ = aryl or alkyl, such as methyl or phenyl;
$R_4$ = arylene, alkylene, or alkyleneoxy, such as phenylene, $(CH_2)_n$, or $(CH_2CH_2O)_n$;
Z = $SO_2$ or C = O; and
X = halogen, preferably fluorine or chlorine.

The resulting polymers are deemed to display a number of useful properties. When crown ethers are the macrocyclic component the materials have the ability to form complexes with such appropriate partners as metal ions or electron acceptors (such as paraquat). Utility in membrane separations and transport is also envisioned. Admixture of the polymer compositions with entangling agents which can penetrate the cavities of the macrocyclic moiety can bring about property enhancement in polymers of relatively low molecular weight as a result of increased molecular entanglements. The polymer compositions described herein should also promote the blending of dissimilar polymers by means of both entanglement and specific interaction mechanisms. Interpenetrating structures can be made in cases where the ring size is sufficient to allow threading. The threading may take place with the segment formed from the BB comonomer or with a separate polymer molecule either prior to, during, or after polymerization.

The present invention is illustrated by the Examples which follow.

EXAMPLE 1

This Example describes the polycondensation of bis(5-carboxy-1,3-phenylene)-32-crown-10, a diacid crown, with bisphenol-A to form a poly(ester crown) in accordance with one embodiment of the present invention.

A solution of tosyl chloride (1.24 gm, 6.5 mmol) in pyridine (5 mL) and N,N-dimethylformamide (15 drops) was maintained at room temperature for thirty minutes and was then added to the diacid crown (1.56 gm, 2.5 mmol) in pyridine (5 mL). The mixture was maintained at room temperature for ten minutes and then at 120° C. for ten minutes. To this solution the bisphenol-A (0.570 gm, 2.5 mmol) in pyridine (5 mL) was added dropwise over twenty minutes at 120° C. The reaction was maintained at 120° C. for three hours. The polymer was isolated by precipitation with methanol. The precipitate was filtered and then washed with water and methanol. The polymer was dried, under vacuum at 45° C. for twenty-four hours, 2.0 gm, yield 100%.

The following characterization data was obtained for the polymer:
$^1$H NMR (DMF-$d_7$/TMS, room temperature): δ8.1 and 3.0-2.6 (DMF), 7.6-6.8 (14H, m, Ph—H), 4.4-3.50 (32H, m, O—$CH_2$), 3.45 (2H, s, $H_2O$ in DMF-d;), 1.70 (6H, s, $CH_3$). IR (KBr pellet): 1737 (C=O), 1600 and 1505 (C=C aromatics), 1129 (C—O—C) cm$^{-1}$. Glass transition temperature ($T_g$): 65° C.; TGA: 5% weight loss at 353° C. in air and 352° C. in nitrogen.

This poly(ester crown) was soluble in $CHCl_3$, $CH_2Cl_2$, tetrahydrofuran, dimethylformamide, dimethylsulfoxide, and pyridine but not in methanol or water. It was white and fibrous and formed a transparent and flexible film from solution. Gel permeation chromatography of this poly(ester crown) in a comparison with a polystyrene standard in chloroform at 30° C. gave a $M_n$ of 55,700 and a $M_W$ of 133,000 with a polydispersity ($M_W/M_n$) of 2.32. Low angle laser light scattering of the polymer gave a molecular weight ($M_W$) of 91,700. This poly(ester crown) has a narrower molecular weight distribution ($M_W/M_n=2.3$) than other aromatic polyesters ($M_W/M_n>3$) prepared under similar conditions (see F. Higashi et al., J. Polym. Sci., Polym. Chem. Ed., 1984, 22, 1653).

EXAMPLE 2

This Example illustrates the polycondensation of bis(5-carboxy-1,3-phenylene)-32-crown-10, a diacid crown, and 4,4'-oxydianiline (abbreviated "4,4'-ODA") to form a poly(amide crown) in accordance with one embodiment of the present invention.

A mixture of 4,4'-ODA (0.5 gm, 2.5 mmol), diacid crown (1.55 gm, 2.5 mmol), lithium chloride (0.25 gm, 5.9 mmol), pyridine (1.25 mL), triphenyl phosphite (1.56 gm, 5.05 mmol), and N-methylpyrrolidone (5 mL) was heated at 100° C. for three hours under nitrogen. The polymer was isolated by precipitation with methanol. The precipitate was filtered and then washed with methanol and dried in vacuo. The polymer was swelled in dimethylacetamide and reprecipitated from methanol one more time, filtered, dried in vacuo at 50° C. to a hard solid polymer, 2.0 gm (100%).

The polymer was not soluble in any solvent. The following characterization data was obtained: Cross polarization magic angle spinning $^{13}$C NMR $\delta$ 165.8 (C=O), 160.4, 136.8, 121.8, 108.6, 104.3 (aromatics), 70.3 (OCH$_2$); FTIR (KBr pellet), 3300 (N—H), 1660 (C=O), 1122 (C—O—C) cm$^{-1}$. Glass transition temperature ($T_g$), 114.5° C., (10° C./min). TGA, 5% weight loss at 366° C. and 325° C. in nitrogen and air, respectively.

EXAMPLE 3

This Example illustrates the synthesis of bis(5-carbomethoxy-1,3-phenylene)-26-crown-8 which can be used as a monomer in the synthesis of poly(ester) and poly(amide crowns) or to bind cations, especially large ones such as diquat.

Triethylene glycol dichloride (10.67 gm, 57 mmol), which was distilled over calcium hydride, in 250 ml dimethylformamide was added to 225 ml of dimethylformamide containing 9.58 gm (57 mmol) of methyl 3,5-dihydroxybenzoate and 2.76 gm (115 mmol) of sodium hydride. The solution was stirred vigorously at 85° C. for forty-eight hours, under a blanket of nitrogen, cooled, filtered and evaporated to give a brown viscous oily residue, which was chromatographed on silica gel (7 gm per 1 gm crude products) with diethyl ether as eluent to produce bis(5-carbomethoxy-1,3-phenylene)-26-crown-8 as a crystalline solid, 1.0 gm, 6% yield, mp 131.2–133.2° C., IR (KBr pellet) 1723 (C=O), 1607 (C=C) and 1129 (C—O—C) cm$^{-1}$; $^1$H NMR (CDCl$_3$/TMS) d 7.15 (4H, d, Ph—H$_{4,6}$), 6.67 (2H, s, Ph—H$_{4,6}$), 4.12 (8H, $\alpha$-OCH$_2$), 3.87 (14H, m, $\beta$-OCH$_2$ and CH$_3$) and 3.75 (8H, s, $\gamma$-OCH$_2$); m/z (EI+): 564 (M+) and 533 (M+-CH$_3$O). Anal. Calcd. for C$_{28}$H$_{36}$O$_{12}$ (MW 564): C, 59.56; H, 6.43. Found: C, 59.38; H, 6.49. Thermal gravimetric analysis (TGA) 5% weight loss at 293° C. in air.

EXAMPLE 4

This Example illustrates the synthesis of bis(5-carbomethoxy-1,3-phenylene)-20-crown-6 which can be used as a monomer in the synthesis of poly(ester) and poly(amide crowns) or to bind cations, especially larger ones such as diquat.

Diethylene glycol dichloride (8.20 gm, 57 mmol) (distilled over calcium hydride) in 250 ml dimethylformamide was added to 225 ml of dimethylformamide containing 9.58 gm (57 mmol) of methyl 3,5-dihydroxybenzoate and 4.6 gm (15 mmol) of potassium hydride. The solution was stirred vigorously at 85° C. for forty-eight hours, under a blanket of nitrogen, cooled, filtered and evaporated to give a brown viscous oily residue, which was chromatographed on silica gel (7 gm per I gm crude products) with diethyl ether as eluent to produce bis(5-carbomethoxy-1,3-phenylene)-20-crown-6 as a crystalline solid, 2.5 gm, 19% yield, mp 179°–181° C., IR (KBr pellet) 1723 (C=O), 1607 (C=C) and 1142 (C—O—C) cm$^{-1}$; $^1$H NMR (CDCl$_3$/TMS) $\delta$ 7.10–7.25 (4H, m, Ph—H$_{4,6}$), 6.75 (2H, m, Ph—H$_2$), 4.15 (8H, m, $\alpha$-OCH$_2$) and 3.87 (14H, m, $\beta$-OCH$_2$ and CH$_3$); m/z (EI+): 476 (M+) and 445 (M+—CH$_3$O).

The foregoing Examples are set forth for illustrative purposes only and should not be construed in a limiting sense. The scope of protection sought is set forth in the claims which follow.

We claim:

1. A bis(extraannular functionally-substituted 1,3-phenylene) crown compound, wherein the functional substituent is selected from the group consisting of carboxy, —NH$_2$, hydroxy, isocyanate, and —CH$_2$OH.

2. A bis(extraannular functionally-substituted 1,3-phenylene) crown compound, wherein the functional substituent is in the 5-position on each phenylene group and is selected from the group consisting of carboxy, —NH$_2$, hydroxy, isocyanate, and —CH$_2$OH.

* * * * *